US009133137B2

(12) United States Patent
Tung

(10) Patent No.: US 9,133,137 B2
(45) Date of Patent: *Sep. 15, 2015

(54) DERIVATIVES OF GEFITINIB

(75) Inventor: Roger Tung, Lexington, MA (US)

(73) Assignee: Concert Pharmaceuticals, Inc., Lexington, MA (US)

(*) Notice: Subject to any disclaimer, the term of this patent is extended or adjusted under 35 U.S.C. 154(b) by 1219 days.

This patent is subject to a terminal disclaimer.

(21) Appl. No.: 12/946,856

(22) Filed: Nov. 15, 2010

(65) Prior Publication Data
US 2011/0059046 A1 Mar. 10, 2011

Related U.S. Application Data

(63) Continuation of application No. 12/358,238, filed on Jan. 22, 2009, now Pat. No. 7,855,204.

(60) Provisional application No. 61/140,073, filed on Dec. 22, 2008, provisional application No. 61/022,806, filed on Jan. 22, 2008.

(51) Int. Cl.
C07D 239/94 (2006.01)
C07D 413/12 (2006.01)
A61K 38/00 (2006.01)

(52) U.S. Cl.
CPC ............ C07D 239/94 (2013.01); C07D 413/12 (2013.01); A61K 38/00 (2013.01)

(58) Field of Classification Search
CPC ..................... C07D 239/94; C07D 413/12
See application file for complete search history.

(56) References Cited

U.S. PATENT DOCUMENTS

| 4,070,289 | A | 1/1978 | Akcasu |
| 6,221,335 | B1 | 4/2001 | Foster |
| 6,258,951 | B1 | 7/2001 | Lohmann et al. |
| 6,440,710 | B1 | 8/2002 | Keinan et al. |
| 6,603,008 | B1 | 8/2003 | Ando et al. |
| 7,517,990 | B2 | 4/2009 | Ito et al. |
| 7,598,273 | B2 | 10/2009 | Gant et al. |
| 7,855,204 | B2 * | 12/2010 | Tung .................... 514/234.5 |
| 2004/0152759 | A1 | 8/2004 | Abrams et al. |
| 2004/0158065 | A1 | 8/2004 | Barth et al. |
| 2007/0082929 | A1 | 4/2007 | Gant et al. |
| 2007/0197695 | A1 | 8/2007 | Potyen et al. |
| 2007/0219203 | A1 | 9/2007 | Bakthavatchalam et al. |
| 2008/0103122 | A1 | 5/2008 | Veltri |
| 2009/0185999 | A1 * | 7/2009 | Tung .................... 424/85.7 |

FOREIGN PATENT DOCUMENTS

| WO | WO-95/26325 | 10/1995 |
| WO | WO-96/33980 | 10/1996 |
| WO | WO-2007/118651 | 10/2007 |

OTHER PUBLICATIONS

FDA Alert for Healthcare Professionals, Gefitinib (marketed as Iressa), 2005.*
Remon et al. Cancer Treatment Reviews 2014, 40, 93-101.*
Maurel et al. Int. J. Radiation Oncology Biol. Phys., vol. 66, No. 5, pp. 1391-1398, 2006.*
Fountzilas et al. J Clin Oncol 2007 (Meeting Abstracts), 25, 15016.*
Moore et al. J Clin Oncol 2007; 25: 1960-1966, abstract.*
Ignatiadis et al. Oncology, 71, 159-163, 2006, abstract.*
Czito et al. J. Clin. Oncol 24, 656-662, 2006.*
Kawada et al., *Kagakuryoho no Ryoiki*, vol. 18, No. 12, pp. 1813-1820 (2002).
Notice of Reasons for Rejection mailed Mar. 28, 2012, in corresponding Japanese Application No. 2010-544356 (with English translation).
Final Rejection mailed Oct. 2, 2012, in corresponding Japanese Application No. 2010-544356 (English translation).
Bergin et al., "Synthesis of isotopomers of gefitinib" (Abstract), Synthesis and applications of isotopically labelled compounds, Proceedings of the International Symposium, 8th, Boston, MA, United States, Jun. 1-5, 2003, pp. 301-304 (2004).
Zhao et al., "Specific method for determination of gefitinib in human plasma, mouse plasma and tissues using high performance liquid chromatography coupled to tandem mass spectrometry", Journal of Chromatography B, 819(1):73-80 (2005).
Concert Pharmaceuticals et al., "Precision Deuterium Chemistry Backgrounder", 2007, pp. 1-6, retrieved from the Internet: URL: http://www.webcitation.org/5e81SGCnI.
Supplemental European Search Report mailed Aug. 5, 2011 in corresponding European Patent Application No. 09703515.8.
Foster, A.B., "Deuterium isotope effects in studies of drug metabolism", TIPS 524-527 (Dec. 1984).
Gouyette, A., Biomedical and Environmental Mass Spectrometry, vol. 15, 243-247 (1988).
Cherrah, Y. et al., Biomedical and Environmental Mass Spectrometry, vol. 14, Issue 11, pp. 653-657 (1987).
Dyck, L.E. et al., Journal of Neurochemistry, vol. 46, Issue 2, pp. 399-404 (1986).
Tonn, G.R., et al., Biological Mass Spectrometry, vol. 22, Issue 11, pp. 633-642 (1993).
Haskins, N.J., Biomedical Spectrometry, vol. 9, Issue 7, pp. 269-277 (1982).
Wolen, R.L., J. Clin. Pharmacology 26: 419-424 (1986).
Pieniaszek, H.J. et al., J. Clin. Pharmacol. 39:817-825 (1999).
Honma, S. et al., Drug Metab Dispos 15(4): 551-559 (1987).
Browne, T.R., Journal of Clinical Pharmacology 38: 213-220 (1998).
Baillie, T.A., Pharmacology Rev. 33:81-132 (1981).
International Search Report and Written Opinion dated Mar. 18, 2009, in corresponding PCT Patent Application No. PCT/US09/00482.

(Continued)

*Primary Examiner* — Matthew Coughlin
(74) *Attorney, Agent, or Firm* — Locke Lord LLP; Jeffrey D. Hsi

(57) ABSTRACT

This invention relates to novel quinazoline derivatives, their derivatives, pharmaceutically acceptable salts thereof. This invention also provides compositions comprising a compound of this invention and the use of such compositions in methods of treating diseases and conditions that are beneficially treated by inhibiting cell surface tyrosine receptor kinases.

1 Claim, 1 Drawing Sheet

(56) References Cited

OTHER PUBLICATIONS

Foster, A.B., Advances in Drug Research, vol. 14, pp. 1-40 (1985).
Prescribing Information for IRESSA (gefitinib), accessed at http://www.accessdata.fda.gov/drugsatfda_docs/label/2005/021399s0081b1.pdf, 2005.
Bai et al., Journal of Liquid Chromatography & Related Technologies, 27(17): 2743-2758 (2004).
Jordan, V.C., Nature Reviews: Drug Discovery, 2:205-213 (2003).
McKillop et al., Xenobiotica 34:917-934 (2004).
McKillop et al., Xenobiotica 34:983-1000 (2004).
McKillop et al., Xenobiotica 35:39-50 (2005).
Kushner et al, Canadian Journal of Physiology and Pharmacology 77: 79-88 (1999).
Fisher et al., Current Opinion in Drug Discovert & Development 9: 101-109 (2006).
Shah et al., J. Oncol. Pharm. Practice 9:151-160 (2003).
Luo et al., Cell 136:823-837 (2009).
Surve et al., "Metabolite Characterization of Anti-cancer Agent Gefitinib in Human Hepatocytes", Drug Metabolism Letters, 7, 126-136 (2013).

* cited by examiner

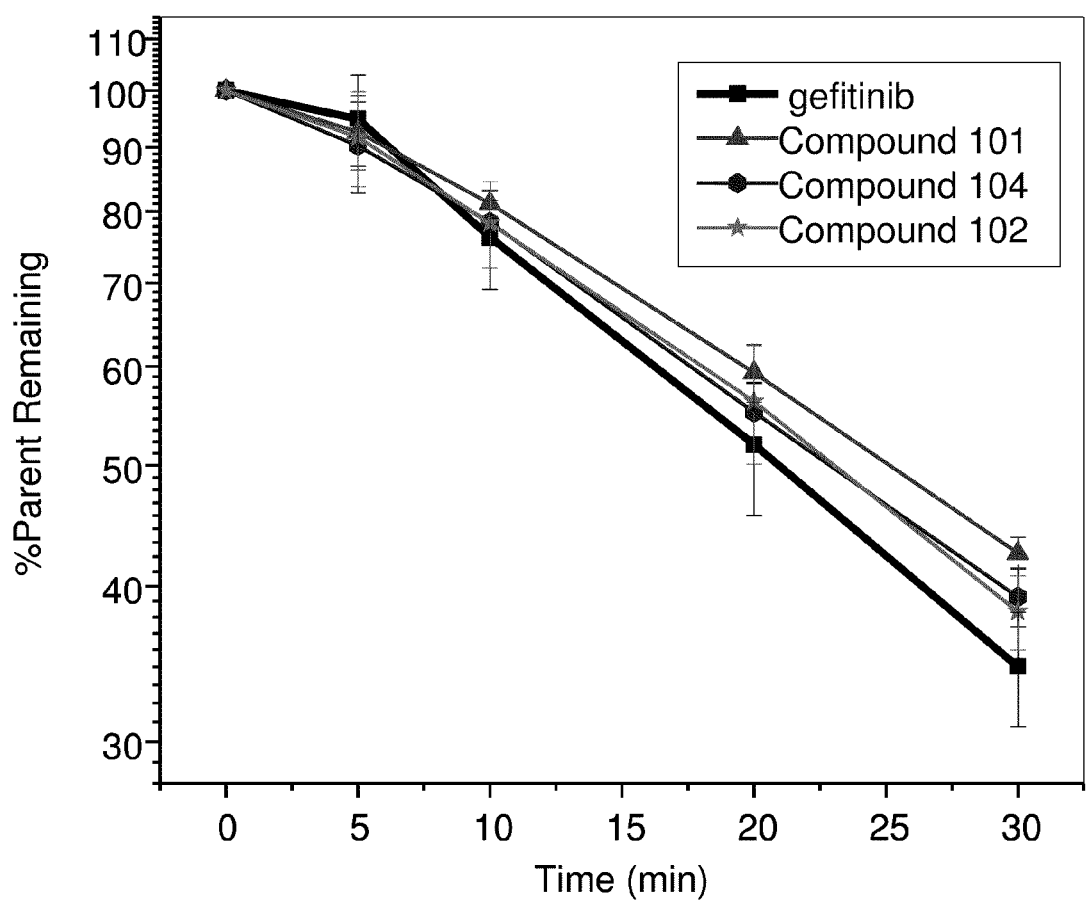

DERIVATIVES OF GEFITINIB

CROSS-REFERENCE TO RELATED APPLICATIONS

This application is a continuation of U.S. patent application Ser. No. 12/358,238, filed Jan. 22, 2009, now allowed, which claims the benefit of U.S. Provisional Patent Application Ser. Nos. 61/022,806, filed Jan. 22, 2008, and 61/140,073, filed Dec. 22, 2008. The contents of each of these applications are incorporated herein by reference in their entirety.

This invention relates to novel quinazoline derivatives, their derivatives, and pharmaceutically acceptable salts thereof. This invention also provides compositions comprising a compound of this invention and the use of such compositions in methods of treating diseases and conditions that are beneficially treated by inhibiting cell surface tyrosine receptor kinases.

Gefitinib, also known as (3-chloro-4-fluoro-phenyl)-[7-methoxy-6-(3-morpholin-4-yl-propoxy)-quinazolin-4-yl]-amine; 4-(3'-chloro-4'-fluoroanilino)-7-methoxy-6-(3-morpholinopropoxy)quinazoline; and Iressa®, modulates EGF type receptor tyrosine kinases (EGFR-TK) (see U.S. Pat. No. 5,770,599).

Gefitinib is currently approved in the United States and Japan for the treatment of non-small cell lung cancer. It is also in clinical trials as either a single agent or as part of a combination treatment for various other cancers including ovarian cancer, bladder cancer, colorectal cancer, head and neck cancer, brain cancer, endocrine cancer, prostate cancer, sarcoma, myeloid leukemia, solid tumors, small cell lung cancer, astrocytoma, breast cancer, squamous cell carcinoma, pancreatic cancer, glioblastoma multiforme, renal cancer, gastric cancer, cancer of unspecified body location/system, and liver cancer.

Gefitinib is known to cause high incidence of diarrhea and rash at approved dosages. Gefitinib has also been linked to pulmonary toxicity in a small percentage of patients (see FDA label—http://www.astrazeneca-us.com/pi/iressa.pdf).

Tyrosine kinase inhibitors, such as gefitinib, are also known to less effective in smokers, as opposed to non-smokers due to more rapid metabolism by the former. Lynch T J et al, N Engl Med 2004, 350:2129-2139; Pao W et al, Proc Natl Acad Sci USA 2004, 101:13306-13311; Marchetti A et al, J Clin Oncol 2005, 23:857-865; Shigematsu H et al, J Natl Cancer Inst 2005, 97:339-346; and Pham D et al, J Clin Oncol 2006, 24: 1700-1704.

Despite the beneficial activities of gefitinib, there is a continuing need for new compounds to treat the aforementioned diseases and conditions.

LIST OF FIGURES

FIG. 1 depicts in vitro $t_{1/2}$ data for compounds 101, 102, and 104 compared to gefitinib.

DEFINITIONS

The terms "ameliorate" and "treat" are used interchangeably and include both therapeutic treatment and prophylactic treatment (reducing the likelihood of development). Both terms mean decrease, suppress, attenuate, diminish, arrest, or stabilize the development or progression of a disease (e.g., a disease or disorder delineated herein), lessen the severity of the disease or improve the symptoms associated with the disease.

"Disease" means any condition or disorder that damages or interferes with the normal function of a cell, tissue, or organ.

It will be recognized that some variation of natural isotopic abundance occurs in a synthesized compound depending upon the origin of chemical materials used in the synthesis. Thus, a preparation of gefitinib will inherently contain small amounts of deuterated isotopologues. The concentration of naturally abundant stable hydrogen isotopes, notwithstanding this variation, is small and immaterial as compared to the degree of stable isotopic substitution of compounds of this invention. See, for instance, Wada, E et al., Seikagaku, 1994, 66: 15; Ganes, L Z et al., Comp Biochem Physiol Mol Integr Physiol, 1998, 119: 725.

The compounds of the present invention are distinguished from such naturally occurring minor forms in that the term "compound" as used in this invention refers to a composition of matter that has a minimum isotopic enrichment factor at least 3000 (45% deuterium incorporation) for each deuterium atom that is present at a site designated as a site of deuteration in Formula (I).

In the compounds of the invention, any atom not specifically designated as a particular isotope is meant to represent any stable isotope of that atom unless otherwise stated. Unless otherwise stated, when a position is designated specifically as "H" or "hydrogen," the position is understood to have hydrogen at its natural abundance isotopic composition. Also unless otherwise stated, when a position is designated specifically as "D" or "deuterium", the position is understood to have deuterium at an abundance at least 3000 times the natural abundance of deuterium, which is 0.015% (i.e., at least 45% deuterium incorporation).

The term "isotopic enrichment factor" as used herein means the ratio between the isotopic abundance and the natural abundance of a specified isotope.

In other embodiments, a compound of this invention has an isotopic enrichment factor for each deuterium present at a site designated as a potential site of deuteration on the compound of at least 3500 (52.5% deuterium incorporation), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

The structural formula depicted herein may or may not indicate whether atoms at certain positions are isotopically enriched. In a most general embodiment, when a structural formula is silent with respect to whether a particular position is isotopically enriched, it is to be understood that the stable isotopes at the particular position are present at natural abundance, or, alternatively, that that particular position is isotopically enriched with one or more naturally occurring stable isotopes. In a more specific embodiment, the stable isotopes are present at natural abundance at all positions in a compound not specifically designated as being isotopically enriched.

The term "isotopologue" refers to a species that differs from a specific compound of this invention only in the isotopic composition thereof. Isotopologues can differ in the level of isotopic enrichment at one or more positions and/or in the positions(s) of isotopic enrichment.

The term "compound," when referring to a compound of this invention, refers to a collection of molecules having an identical chemical structure, except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this invention will depend upon a number of factors including the isotopic purity of deuterated reagents used to make the compound and the efficiency of incorporation of deuterium in the various synthesis steps used to prepare the compound. However, as set forth above the relative amount of such isotopologues in toto will be less than 55% of the compound. In other embodiments, the relative amount of such isotopologues in toto will be less than 50%, less than 47.5%, less than 40%, less than 32.5%, less than 25%, less than 17.5%, less than 10%, less than 5%, less than 3%, less than 1%, or less than 0.5% of the compound.

The invention also provides salts, of the compounds of the invention.

A salt of a compound of this invention is formed between an acid and a basic group of the compound, such as an amino functional group, or a base and an acidic group of the compound, such as a carboxyl functional group. According to another embodiment, the compound is a pharmaceutically acceptable acid addition salt.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

The compounds of the present invention (e.g., compounds of Formula I), may contain an asymmetric carbon atom, for example, as the result of deuterium substitution or otherwise. As such, compounds of this invention can exist as either individual enantiomers, or mixtures of the two enantiomers. Accordingly, a compound of the present invention will include both racemic mixtures, and also individual respective stereoisomers that are substantially free from another possible stereoisomer. The term "substantially free of other stereoisomers" as used herein means less than 25% of other stereoisomers, preferably less than 10% of other stereoisomers, more preferably less than 5% of other stereoisomers and most preferably less than 2% of other stereoisomers, or less than "X"% of other stereoisomers (wherein X is a number between 0 and 100, inclusive) are present. Methods of obtaining or synthesizing an individual enantiomer for a given compound are well known in the art and may be applied as practicable to final compounds or to starting material or intermediates.

The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"D" refer to deuterium. "Stereoisomer" refers to both enantiomers and diastereomers.

The term "smoker" as used herein means a human that has a smoking history of more than 15 pack-years and who has smoked in the past 25 years. The term "non-smoker" as used herein means a human that has a smoking history of 15 pack years or less, or who has not smoked for over 25 years. A "pack-year" is calculated by multiplying the number of cigarettes smoked per day by the number of years smoked and dividing that product by 20 (see http://www.cancer.gov/Templates/db_alpha.aspx?CdrID=306510).

Throughout this specification, a variable may be referred to generally (e.g., "each R") or may be referred to specifically (e.g., $R^1$, $R^2$, $R^3$, etc.). Unless otherwise indicated, when a variable is referred to generally, it is meant to include all specific embodiments of that particular variable.

Therapeutic Compounds

The present invention provides a compound of Formula A:

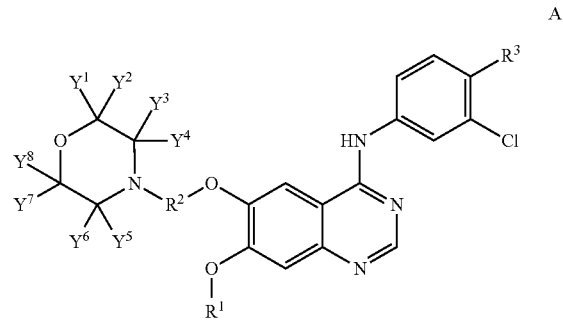

or a pharmaceutically acceptable salt thereof, wherein:
$R^1$ is selected from H, $CH_3$, $CH_2D$, $CHD_2$ and $CD_3$;
$R^2$ is n-propylene, wherein 1 to 6 hydrogen atoms are optionally replaced with deuterium atoms;
$R^3$ is selected from: F, Cl, Br, H, OH, F, $OCD_3$, or $OCH_3$
each Y (i.e., each of $Y^1$-$Y^8$) is independently selected from hydrogen and deuterium; and when $R^1$ is H or $CH_3$, and $R^2$ is $(CH_2)_3$, then at least one Y is deuterium.

The present invention also provides a compound of Formula I:

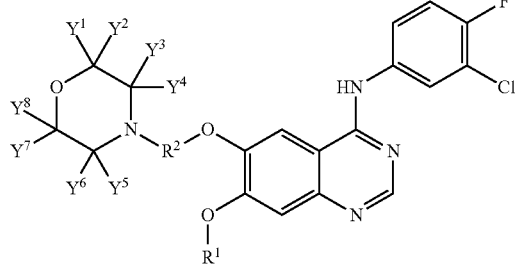

or a pharmaceutically acceptable salt thereof, wherein:
$R^1$ is selected from H, $CH_3$, $CH_2D$, $CHD_2$ and $CD_3$;
$R^2$ is n-propylene, wherein 1 to 6 hydrogen atoms are optionally replaced with deuterium atoms;
each Y (i.e., each of $Y^1$-$Y^8$) is independently selected from hydrogen and deuterium; and
when $R^1$ is H or $CH_3$, and $R^2$ is $(CH_2)_3$, then at least one Y is deuterium.

In one embodiment of a compound of Formula A or I:
$R^1$ is selected from H, $CH_3$, and $CD_3$;
$R^2$ is selected from $(CH_2)_3$, $CD_2CH_2CD_2$, $CD_2CH_2CH_2$, $CD_2CD_2CH_2$, $CH_2CD_2CH_2$, $CH_2CD_2CD_2$, $CH_2CH_2CD_2$, and —$(CD_2)_3$; and
$Y^1$, $Y^2$, $Y^7$, and $Y^8$ are the same; and $Y^3$, $Y^4$, $Y^5$, and $Y^6$ are the same.

In another embodiment of a compound of Formula A or I:
$R^1$ is selected from $CH_3$, and $CD_3$;
$R^2$ is selected from $(CH_2)_3$, and —$(CD_2)_3$; and
$Y^1$-$Y^8$ are the same.

In certain embodiments of Formula A or I:
a) $R^1$ is selected from H, $CH_3$ and $CD_3$;
b) $R^2$ is selected from $(CH_2)_3$, $CD_2CH_2CD_2$, $CD_2CH_2CH_2$, $CD_2CD_2CH_2$, $CH_2CD_2CH_2$, $CH_2CD_2CD_2$, $CH_2CH_2CD_2$, and —$(CD_2)_3$; or
c) $Y^1$, $Y^2$, $Y^7$ and $Y^8$ are the same; and $Y^3$, $Y^4$, $Y^5$ and $Y^6$ are the same.

In a more specific embodiment, a compound of Formula A or I has the features of two or more of a) to c) above.

In other specific embodiments of Formula A or I:
a1) $R^1$ is selected from $CH_3$ and $CD_3$;
b1) $R^2$ is selected from $(CH_2)_3$, and —$(CD_2)_3$; or
c1) each Y is the same.

In a more specific embodiment, a compound of Formula A or I has the features of two or more of a1) to c1). In another more specific embodiment a compound of Formula A or I has the features of two or more of a) or a1), b) or b1); and c) or c1).

In yet another embodiment, the compound is selected from any one of the compounds set forth in Table 1, below:

TABLE 1

| Cmpd | $Y^1$=$Y^2$ | $Y^3$=$Y^4$ | $Y^5$=$Y^6$ | $Y^7$=$Y^8$ | $R^1$ | $R^2$ | $R^3$ |
|---|---|---|---|---|---|---|---|
| 101 | D | D | D | D | $CD_3$ | $CD_2CD_2CD_2$ | F |
| 102 | H | H | H | H | $CD_3$ | $CD_2CD_2CD_2$ | F |
| 103 | D | D | D | D | $CD_3$ | $CH_2CH_2CH_2$ | F |
| 104 | H | H | H | H | $CD_3$ | $CH_2CH_2CH_2$ | F |
| 105 | D | D | D | D | $CD_3$ | $CD_2CD_2CD_2$ | F |

TABLE 1-continued

| Cmpd | $Y^1$=$Y^2$ | $Y^3$=$Y^4$ | $Y^5$=$Y^6$ | $Y^7$=$Y^8$ | $R^1$ | $R^2$ | $R^3$ |
|---|---|---|---|---|---|---|---|
| 106 | H | H | H | H | $CD_3$ | $CD_2CD_2CD_2$ | F |
| 107 | D | D | D | D | $CD_3$ | $CH_2CH_2CH_2$ | F |
| 108 | D | D | D | D | $CD_3$ | $CD_2CD_2CD_2$ | H |
| 109 | H | H | H | H | $CD_3$ | $CD_2CD_2CD_2$ | H |
| 110 | D | D | D | D | $CD_3$ | $CH_2CH_2CH_2$ | H |
| 111 | H | H | H | H | $CD_3$ | $CH_2CH_2CH_2$ | H |
| 112 | D | D | D | D | $CD_3$ | $CD_2CD_2CD_2$ | H |
| 113 | H | H | H | H | $CD_3$ | $CD_2CD_2CD_2$ | H |
| 114 | D | D | D | D | $CD_3$ | $CH_2CH_2CH_2$ | H |
| 115 | D | D | D | D | $CD_3$ | $CD_2CD_2CD_2$ | OH |
| 116 | H | H | H | H | $CD_3$ | $CD_2CD_2CD_2$ | OH |
| 117 | D | D | D | D | $CD_3$ | $CH_2CH_2CH_2$ | OH |
| 118 | H | H | H | H | $CD_3$ | $CH_2CH_2CH_2$ | OH |
| 119 | D | D | D | D | $CD_3$ | $CD_2CD_2CD_2$ | OH |
| 120 | H | H | H | H | $CD_3$ | $CD_2CD_2CD_2$ | OH |
| 121 | D | D | D | D | $CD_3$ | $CH_2CH_2CH_2$ | OH |
| 122 | D | D | D | D | $CD_3$ | $CD_2CD_2CD_2$ | $OCD_3$ |
| 123 | H | H | H | H | $CD_3$ | $CD_2CD_2CD_2$ | $OCD_3$ |
| 124 | D | D | D | D | $CD_3$ | $CH_2CH_2CH_2$ | $OCD_3$ |
| 125 | H | H | H | H | $CD_3$ | $CH_2CH_2CH_2$ | $OCD_3$ |
| 126 | D | D | D | D | $CD_3$ | $CD_2CD_2CD_2$ | $OCD_3$ |
| 127 | H | H | H | H | $CD_3$ | $CD_2CD_2CD_2$ | $OCD_3$ |
| 128 | D | D | D | D | $CD_3$ | $CH_2CH_2CH_2$ | $OCD_3$ |
| 129 | D | D | D | D | $CD_3$ | $CD_2CD_2CD_2$ | $OCH_3$ |
| 130 | H | H | H | H | $CD_3$ | $CD_2CD_2CD_2$ | $OCH_3$ |
| 131 | D | D | D | D | $CD_3$ | $CH_2CH_2CH_2$ | $OCH_3$ |
| 132 | H | H | H | H | $CD_3$ | $CH_2CH_2CH_2$ | $OCH_3$ |
| 133 | D | D | D | D | $CD_3$ | $CD_2CD_2CD_2$ | $OCH_3$ |
| 134 | H | H | H | H | $CD_3$ | $CD_2CD_2CD_2$ | $OCH_3$ |
| 135 | D | D | D | D | $CD_3$ | $CH_2CH_2CH_2$ | $OCD_3$ |
| 136 | D | D | D | D | $CD_3$ | $CD_2CD_2CD_2$ | Cl |
| 137 | H | H | H | H | $CD_3$ | $CD_2CD_2CD_2$ | Cl |
| 138 | D | D | D | D | $CD_3$ | $CH_2CH_2CH_2$ | Cl |
| 139 | H | H | H | H | $CD_3$ | $CH_2CH_2CH_2$ | Cl |
| 140 | D | D | D | D | $CD_3$ | $CH_2CH_2CH_2$ | Cl |
| 141 | H | H | H | H | $CD_3$ | $CH_2CH_2CH_2$ | Cl |
| 142 | D | D | D | D | $CD_3$ | $CH_2CH_2CH_2$ | Cl |
| 143 | D | D | D | D | $CD_3$ | $CD_2CD_2CD_2$ | Br |
| 144 | H | H | H | H | $CD_3$ | $CD_2CD_2CD_2$ | Br |
| 145 | D | D | D | D | $CD_3$ | $CH_2CH_2CH_2$ | Br |
| 146 | H | H | H | H | $CD_3$ | $CH_2CH_2CH_2$ | Br |
| 147 | D | D | D | D | $CD_3$ | $CD_2CD_2CD_2$ | Br |
| 148 | H | H | H | H | $CD_3$ | $CD_2CD_2CD_2$ | Br |
| 149 | D | D | D | D | $CD_3$ | $CH_2CH_2CH_2$ | Br |

In another set of embodiments, any atom not designated as deuterium in any of the embodiments set forth above is present at its natural isotopic abundance.

The synthesis of compounds of Formula I can be readily achieved by synthetic chemists of ordinary skill Relevant procedures and intermediates are disclosed, for instance in PCT Publication WO 96/33980, PCT Publication WO 2005/023783, PCT Publication WO 2005/070909, PCT Publication WO 2005/013998; and in Bruno, S M et al., Molecules, 2006, 11: 286-297.

Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure.

EXEMPLARY SYNTHESIS

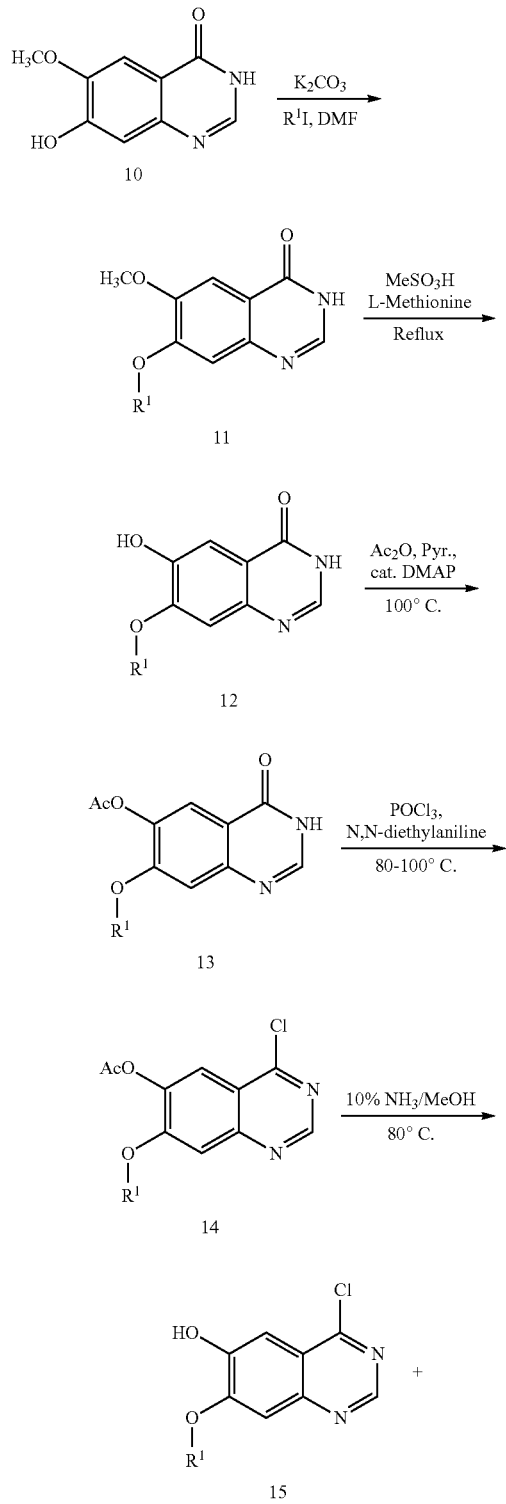

Scheme 1 Synthesis of a Compound of Formula A.

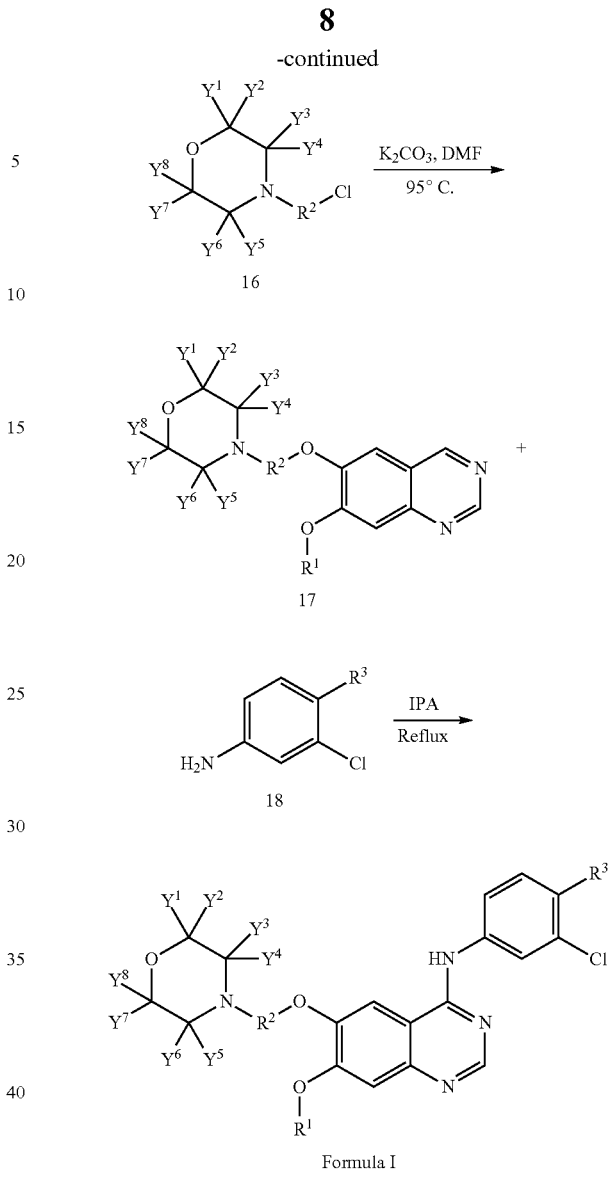

Formula I

A convenient method for synthesizing compounds of Formula A is depicted in Scheme 1 above. Thus, reaction of 10 (synthesized according to Harris, C S et al., Tet Lett, 2005, 46: 1835-1837) with $R^1I$ in the presence of potassium carbonate in DMF provides 11. Demethylation of 11 using acid provides 12. Acetylation of 12 provides 13, which is converted to chloro compound 14 using phosphorous chloride in the presence of an amine base. Deacetylation of 14 provides phenol 15, which is coupled with appropriately deuterated morpholine 16 to provide 17. Reaction of 17 with aniline 18 then provides a compound of Formula A.

Scheme 2a. Synthesis of $16\text{-}d_{14}$.

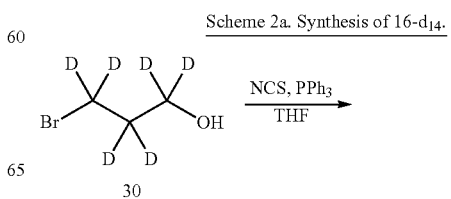

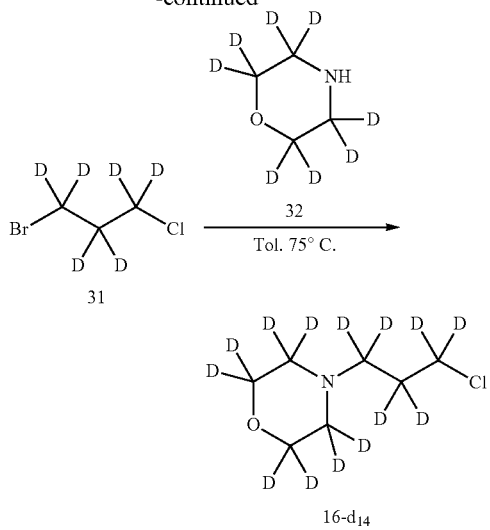

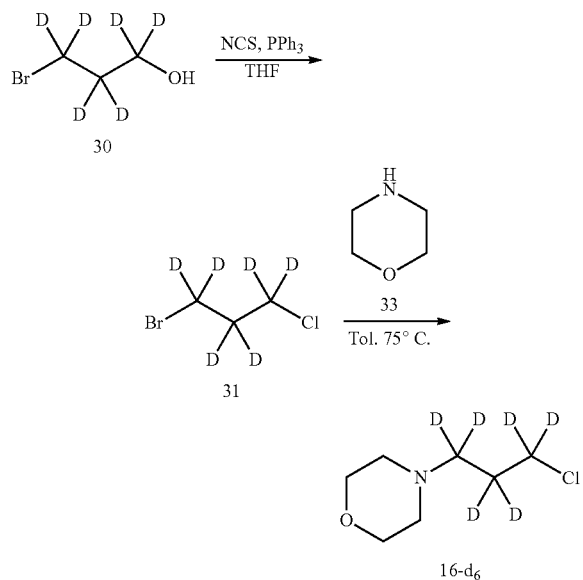

Scheme 2b Scheme 2a. Synthesis of 16-d$_6$.

The synthesis of appropriately deuterated 1-chloropropyl-morpholine 16-d$_{14}$ and 16-d$_6$ is depicted in Schemes 2a and 2b above. Commercially available 3-Bromo-1-propanol-1,1,2,2,3,3-d$_6$ 30 is treated with N-chlorosuccinimide (NCS) and triphenylphosphine to give the corresponding chloride 31 described in James G et al, J Labelled Comp Radiopharm 1988, 25:263-275. The chloride 31 is then treated using the procedure from Syn Comm 2006, 36:347-354 with either commercially available morpholine-2,2,3,3,5,5,6,6-d8 32 in toluene to afford 16-d$_{14}$ or with morpholine 33 in toluene using the procedure from Syn Comm 2006, 36:347-354 to afford 16-d$_6$.

The specific approaches and compounds shown above are not intended to be limiting. The chemical structures in the schemes herein depict variables that are hereby defined commensurately with chemical group definitions (moieties, atoms, etc.) of the corresponding position in the compound formulae herein, whether identified by the same variable name (i.e., R$^1$, R$^2$, R$^3$, etc.) or not. The suitability of a chemical group in a compound structure for use in the synthesis of another compound is within the knowledge of one of ordinary skill in the art.

Additional methods of synthesizing compounds of Formula I and their synthetic precursors, including those within routes not explicitly shown in schemes herein, are within the means of chemists of ordinary skill in the art. Synthetic chemistry transformations and protecting group methodologies (protection and deprotection) useful in synthesizing the applicable compounds are known in the art and include, for example, those described in Larock R, *Comprehensive Organic Transformations*, VCH Publishers (1989); Greene T W et al., *Protective Groups in Organic Synthesis*, 3$^{rd}$ Ed., John Wiley and Sons (1999); Fieser L et al., *Fieser and Fieser's Reagents for Organic Synthesis*, John Wiley and Sons (1994); and Paquette L, ed., *Encyclopedia of Reagents for Organic Synthesis*, John Wiley and Sons (1995) and subsequent editions thereof.

Combinations of substituents and variables envisioned by this invention are only those that result in the formation of stable compounds.

Compositions

The invention also provides pyrogen-free compositions comprising an effective amount of a compound of Formula A or I (e.g., including any of the formulae herein), or a pharmaceutically acceptable salt of said compound; and a pharmaceutically acceptable carrier. Preferably, a composition of this invention is formulated for pharmaceutical use ("a pharmaceutical composition"), wherein the carrier is a pharmaceutically acceptable carrier. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

If required, the solubility and bioavailability of the compounds of the present invention in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of this invention optionally formulated with a poloxamer, such as LUTROL™ and PLURONIC™ (BASF Corporation), or block copolymers of ethylene oxide and propylene oxide. See U.S. Pat. No. 7,014,866; and United States patent publications 20060094744 and 20060079502.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington's Pharmaceutical Sciences, Mack Publishing Company, Philadelphia, Pa. (17th ed. 1985).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In certain embodiments, the compound is administered orally. Compositions of the present invention suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, e.g.: Rabinowitz J D and Zaffaroni A C, U.S. Pat. No. 6,803,031, assigned to Alexza Molecular Delivery Corporation.

Topical administration of the pharmaceutical compositions of this invention is especially useful when the desired treatment involves areas or organs readily accessible by topical application. For topical application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this invention may also be topically applied to the lower intestinal tract by rectal suppository formulation or in a suitable enema formulation. Topically-transdermal patches and iontophoretic administration are also included in this invention.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

Thus, according to yet another embodiment, the compounds of this invention may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the invention provides a method of coating an implantable medical device comprising the step of contacting said device with the coating composition described above. It will be obvious to those skilled in the art that the coating of the device will occur prior to implantation into a mammal.

According to another embodiment, the invention provides a method of impregnating an implantable drug release device comprising the step of contacting said drug release device with a compound or composition of this invention. Implantable drug release devices include, but are not limited to, biodegradable polymer capsules or bullets, non-degradable, diffusible polymer capsules and biodegradable polymer wafers.

According to another embodiment, the invention provides an implantable medical device coated with a compound or a composition comprising a compound of this invention, such that said compound is therapeutically active.

According to another embodiment, the invention provides an implantable drug release device impregnated with or containing a compound or a composition comprising a compound of this invention, such that said compound is released from said device and is therapeutically active.

Where an organ or tissue is accessible because of removal from the patient, such organ or tissue may be bathed in a medium containing a composition of this invention, a composition of this invention may be painted onto the organ, or a composition of this invention may be applied in any other convenient way.

In another embodiment, a composition of this invention further comprises a second therapeutic agent. The second therapeutic agent may be selected from any compound or therapeutic agent known to have or that demonstrates advantageous properties when administered with a compound having the same mechanism of action as gefitinib. Such agents include those useful in the treatment of a patient suffering from or susceptible to cancer.

In one embodiment, the second therapeutic agent is selected from anastrozole, arimidex, cediranib (AZD-2171), bexarotene, calcitriol, capecitabine, carboplatin, cefixime, celecoxib, canertinib (CI-1033), cisplatin, dexamethasone, docetaxel, erbitux, etoposide, everolimus, everolimus, faslodex, fluorouracil, fulvestrant, gemcitabine, irinotecan, leucovorin, loperamide, oxaliplatin, paclitaxel, PEG-interferon alpha, pemetrexed, raltitrexed, simvastatin, sirolimus, sunitinib (SU11248), tamoxifen, temozolomide, topotecan, trastuzumab, and vinorelbine.

In another embodiment, the invention provides separate dosage forms of a compound of this invention and one or more of any of the above-described second therapeutic agents, wherein the compound and second therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the invention, the compound of the present invention is present in an effective amount. As used herein, the term "effective amount" refers to an amount which, when administered in a proper dosing regimen, is sufficient to reduce or ameliorate the severity, duration or progression of the disorder being treated, prevent the advancement of the disorder being treated, cause the regression of the disorder being treated, or enhance or improve the prophylactic or therapeutic effect(s) of another therapy.

The interrelationship of dosages for animals and humans (based on milligrams per meter squared of body surface) is described in Freireich et al., (1966) Cancer Chemother. Rep 50: 219. Body surface area may be approximately determined from height and weight of the patient. See, e.g., Scientific Tables, Geigy Pharmaceuticals, Ardsley, N.Y., 1970, 537.

In one embodiment, an effective amount of a compound of this invention can range from 10-1000 mg/day. In some embodiments, an effective amount ranges from 100-500 mg/day. In other embodiments, an effective amount ranges from 50-250 mg/day. In still other embodiments and effective amount is about 250 mg/day.

Effective doses will also vary, as recognized by those skilled in the art, depending on the diseases treated, the severity of the disease, the route of administration, the sex, age and general health condition of the patient, excipient usage, the possibility of co-usage with other therapeutic treatments such as use of other agents and the judgment of the treating physician. For example, guidance for selecting an effective dose can be determined by reference to the prescribing information for gefitinib.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are incorporated herein by reference in their entirety.

It is expected that some of the second therapeutic agents referenced above will act synergistically with the compounds of this invention. When this occurs, it will allow the effective dosage of the second therapeutic agent and/or the compound of this invention to be reduced from that required in a monotherapy. This has the advantage of minimizing toxic side effects of either the second therapeutic agent of a compound of this invention, synergistic improvements in efficacy, improved ease of administration or use and/or reduced overall expense of compound preparation or formulation.

Methods of Treatment

In another embodiment, the invention provides a method of modulating the activity of an epidermal growth factor receptor tyrosine kinase in a cell, comprising contacting a cell with one or more compounds of Formula A or I herein.

According to another embodiment, the invention provides a method of treating a patient suffering from, or susceptible to, cancer.

In one particular embodiment, the method of this invention is used to treat a patient suffering from or susceptible to a disease or condition selected from non-small cell lung cancer, bladder cancer, head and neck cancer, colorectal cancer, esophageal cancer, metastatic kidney cancer, metastatic pancreatic cancer, prostate cancer, salivary gland cancer, skin cancer, thyroid cancer, adrenocortical carcinoma, glioblastoma multiforme, glioma, acute myeloid leukemia, synovial sarcoma, metastatic breast cancer and solid tumor cancer.

In still another embodiment, the patient suffering from or susceptible to any of the aforementioned diseases or conditions is a smoker. In still another embodiment, the patient suffering from or susceptible to any of the aforementioned diseases or conditions is a non-smoker.

In another particular embodiment, the method of this invention is used to treat a patient suffering from or susceptible to non-small cell lung cancer.

Methods delineated herein also include those wherein the patient is identified as in need of a particular stated treatment. Identifying a patient in need of such treatment can be in the judgment of a patient or a health care professional and can be subjective (e.g. opinion) or objective (e.g. measurable by a test or diagnostic method).

In another embodiment, any of the above methods of treatment comprises the further step of co-administering to the patient one or more second therapeutic agents. The choice of second therapeutic agent may be made from any second therapeutic agent known to be useful for co-administration with gefitinib. The choice of second therapeutic agent is also dependent upon the particular disease or condition to be treated. Examples of second therapeutic agents that may be employed in the methods of this invention are those set forth above for use in combination compositions comprising a compound of this invention and a second therapeutic agent.

In particular, the combination therapies of this invention include co-administering a compound of Formula A or I and a second therapeutic agent for treatment of the following conditions (with the particular second therapeutic agent indicated in parentheses following the indication): bladder cancer (cisplatin, gemcitabine); breast cancer (trastuzumab, tamoxifen, anastrozole, arimidex, CI-1033, docetaxel, faslodex, fulvestrant); colorectal cancer (raltitrexed, oxaliplatin, leucovorin, irinotecan, fluorouracil, capecitabine); esophageal cancer (paclitaxel, oxaliplatin, irinotecan, fluorouracil, cisplatin); gastric cancer (leucovorin, fluorouracil); glioma (temozolomide); head and neck cancer (carboplatin, cisplatin, docetaxel, fluorouracil); kidney cancer (PEG-interferon alpha); lung adenocarcinoma (carboplatin, paclitaxel); nasopharyngeal cancer (celecoxib); neuroblastoma (loperamide); non-small cell lung cancer (AZD2171, bexarotene, carboplatin, celecoxib, cisplatin, docetaxel, Erbitux, everolimus, fulvestrant, gemcitabine, paclitaxel, pemetrexed, simvastatin, sirolimus, vinorelbine); ovarian cancer (anastrozole, topotecan); pancreatic cancer (docetaxel, gemcitabine); prostate cancer (docetaxel, etoposide, everolimus); renal cell carcinoma (SU011248); skin cancer (PEG-interferon alpha); solid tumors (calcitriol, capecitabine, cefixime, dexamethasone, irinotecan, oxaliplatin); urothelial cancer (docetaxel).

The term "co-administered" as used herein means that the second therapeutic agent may be administered together with a compound of this invention as part of a single dosage form (such as a composition of this invention comprising a compound of the invention and an second therapeutic agent as described above) or as separate, multiple dosage forms. Alternatively, the additional agent may be administered prior to, consecutively with, or following the administration of a compound of this invention. In such combination therapy treatment, both the compounds of this invention and the second therapeutic agent(s) are administered by conventional methods. The administration of a composition of this invention, comprising both a compound of the invention and a second therapeutic agent, to a patient does not preclude the separate administration of that same therapeutic agent, any other second therapeutic agent or any compound of this invention to said patient at another time during a course of treatment.

Effective amounts of these second therapeutic agents are well known to those skilled in the art and guidance for dosing may be found in patents and published patent applications referenced herein, as well as in Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the second therapeutic agent's optimal effective-amount range.

In one embodiment of the invention, where a second therapeutic agent is administered to a subject, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

In yet another aspect, the invention provides the use of a compound of Formula A or I alone or together with one or more of the above-described second therapeutic agents in the manufacture of a medicament, either as a single composition or as separate dosage forms, for treatment or prevention in a patient of a disease, disorder or symptom set forth above. Another aspect of the invention is a compound of Formula A or I for use in the treatment or prevention in a patient of a disease, disorder or symptom thereof delineated herein.

Diagnostic Methods and Kits

The present invention also provides kits for use to treat non-small cell lung cancer, bladder cancer, head and neck cancer, colorectal cancer, esophageal cancer, metastatic kidney cancer, metastatic pancreatic cancer, prostate cancer, salivary gland cancer, skin cancer, thyroid cancer, adrenocortical carcinoma, glioblastoma multiforme, glioma, acute myeloid leukemia, synovial sarcoma, metastatic breast cancer and solid tumor cancer. These kits comprise (a) a pharmaceutical composition comprising a compound of Formula A or I or a pharmaceutically acceptable salt, thereof, wherein said pharmaceutical composition is in a container; and (b) instructions describing a method of using the pharmaceutical composition to treat the corresponding cancer.

The container may be any vessel or other sealed or sealable apparatus that can hold said pharmaceutical composition. Examples include bottles, ampules, divided or multi-chambered holders bottles, wherein each division or chamber comprises a single dose of said composition, a divided foil packet wherein each division comprises a single dose of said composition, or a dispenser that dispenses single doses of said composition. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle, which is in turn contained within a box. In one embodiment, the container is a blister pack.

The kits of this invention may also comprise a device to administer or to measure out a unit dose of the pharmaceutical composition. Such device may include an inhaler if said composition is an inhalable composition; a syringe and needle if said composition is an injectable composition; a syringe, spoon, pump, or a vessel with or without volume markings if said composition is an oral liquid composition; or any other measuring or delivery device appropriate to the dosage formulation of the composition present in the kit.

In certain embodiment, the kits of this invention may comprise in a separate vessel of container a pharmaceutical composition comprising a second therapeutic agent, such as one of those listed above for use for co-administration with a compound of this invention.

EXAMPLES

Example 1

Synthesis of 3-(Morpholino-$d_8$)propyl-$d_6$ methanesulfonate (43)

Intermediate 43 was prepared as outlined in Scheme 3 below. Details of the synthesis are as follows.

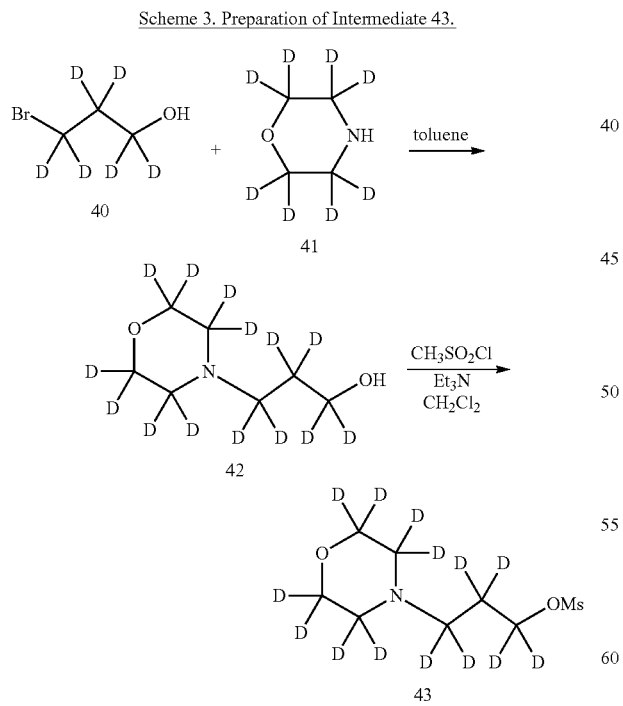

Scheme 3. Preparation of Intermediate 43.

Synthesis of 3-(Morpholino-d8)propan-d6-1-ol (42). To a stirred solution of 3-bromopropanol-$d_6$ 40 (1.5 g, 10.3 mmol) in toluene (15 mL) was added morpholine-$d_8$ 41 (1.96 g, 20.7 mmol) dropwise. The mixture was heated to 80° C. and stirred for 4 hours (h). The resulting suspension was filtered and the filtrate was concentrated under reduced pressure to afford the product 42 (1.5 g, 93%). MS (M+H): 160.2.

Synthesis of 3-(Morpholino-$d_8$)propyl-$d_6$ methanesulfonate (43). To a stirred solution of 42 (1.6 g, 10.0 mmol) in dichloromethane (20 ml) was added triethylamine (2.7 ml, 19.8 mmol) and methanesulfonyl chloride (1.6 ml, 19.8 mmol) dropwise. The reaction mixture was added to a saturated (satd) NaHCO$_3$ solution (10 mL) and the resulting mixture was extracted with dichloromethane. The organic layer was concentrated under reduced pressure to afford the product 43 (2.00 g, 86%). MS (M+H): 238.

Example 2

Synthesis of 3-Morpholino(propyl-$d_6$) methanesulfonate (44)

Intermediate 44 was prepared as outlined in Scheme 3 above using appropriately deuterated starting materials. Details of the synthesis are as follows.

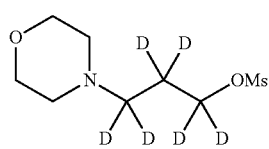

Synthesis of 3-Morpholino(propan-$d_6$)-1-ol. To a stirred solution of 3-bromopropanol-$d_6$ 40 (2.50 g, 17.2 mmol) in toluene (25 mL) was added morpholine (3.00 g, 34.5 mmol) dropwise. The mixture was heated to 80° C. and stirred for 4 hours (h). The resulting suspension was filtered and the filtrate was concentrated under reduced pressure to afford the product (1.50 g, 57%). MS (M+H): 152.

Synthesis of 3-Morpholino(propyl-$d_6$) methanesulfonate (44). To a stirred solution of 3-morpholino(propan-$d_6$)-1-ol (2 g, 13.2 mmol) in dichloromethane (20 ml) was added triethylamine (2.7 ml, 19.8 mmol) and methanesulfonyl chloride (1.6 ml, 19.8 mmol) dropwise. The reaction mixture was added to a satd NaHCO$_3$ solution (10 mL) and the resulting mixture was extracted with dichloromethane. The organic layer was concentrated under reduced pressure to afford the product 44 (2.40 g, 80%). MS (M+H): 230.1

Example 3

Synthesis of 4-(3-Chloropropyl)morpholine (45)

Intermediate 45 was prepared as outlined in Scheme 4 below. Details of the synthesis follow.

Scheme 4. Preparation of Intermediate 45.

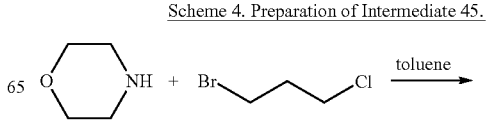

-continued

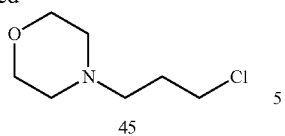
45

Synthesis of 4-(3-Chloropropyl)morpholine (45). To a solution of 1-bromo-3-chloropropane (10.0 g, 63.5 mmol) in toluene (100 mL) was added morpholine (11.0 mL, 127 mmol). The mixture was stirred under reflux conditions for 2 h, then was filtered. The filtrate was washed with water and the organic layer was dried, concentrated in vacuo, then distilled to afford 45 (10.0 g, 96%). $^1$H NMR (300 MHz, DMSO-$d_6$): δ 3.70-3.80(m, 4H), 3.60 (t, 2H), 2.40-2.60(m, 6H), 1.90 (m, 2H). MS (M+H): 164.

Example 4

Synthesis of N-(3-Chloro-4-fluorophenyl)-7-(methoxy-$d_3$)-6-(3-(morpholino-$d_8$)propoxy-$d_6$)quinazolin-4-amine (101)

Compound 101 was prepared as outlined in Scheme 5 below. Details of the synthesis are set forth below.

Scheme 5. Preparation of Compound 101.

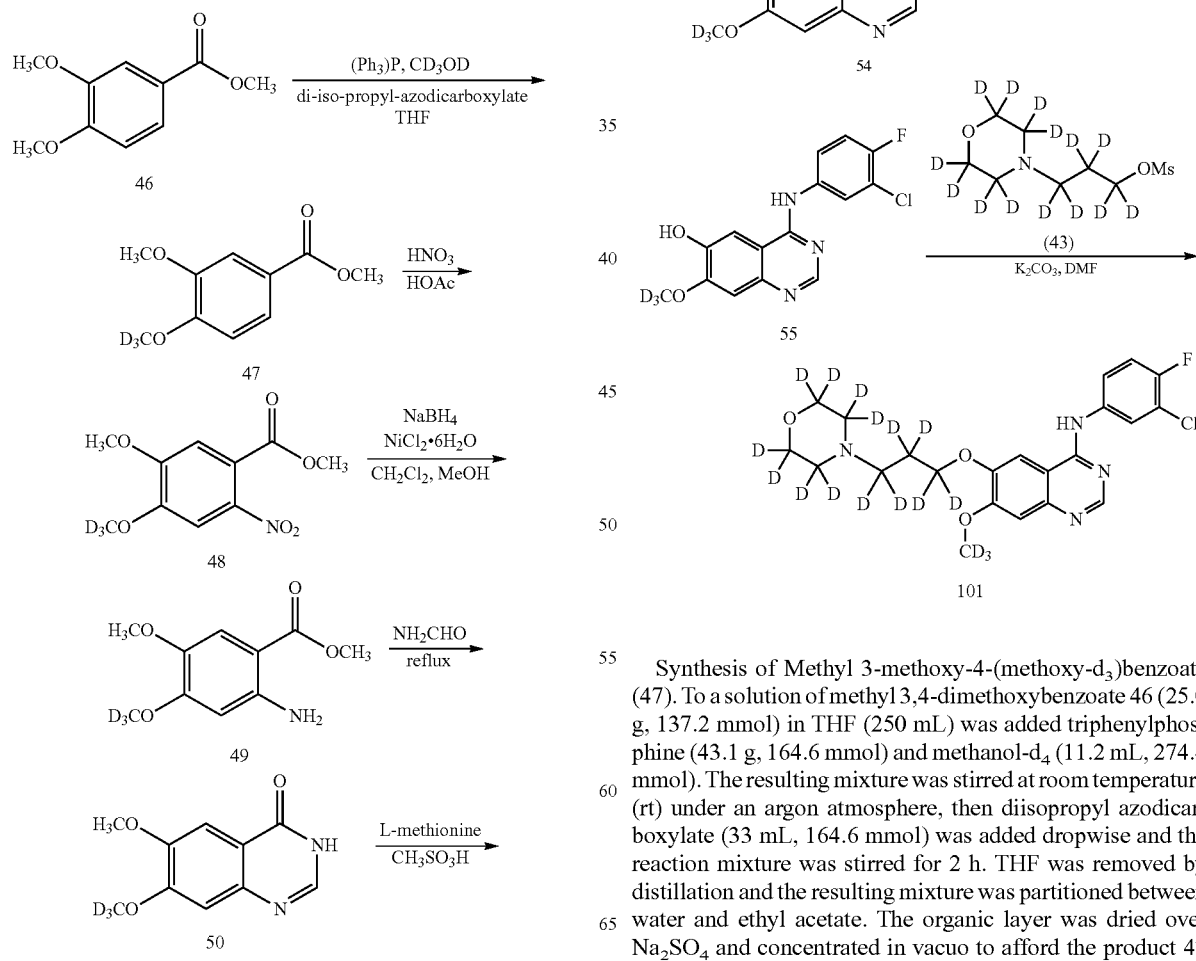

-continued

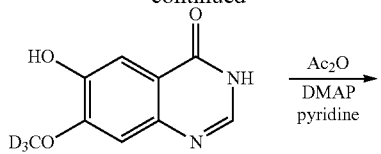
51

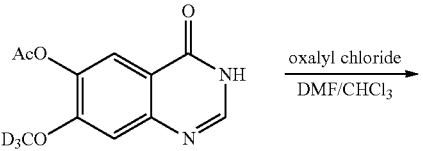
52

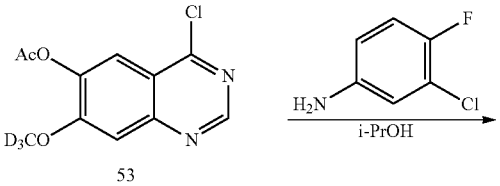
53

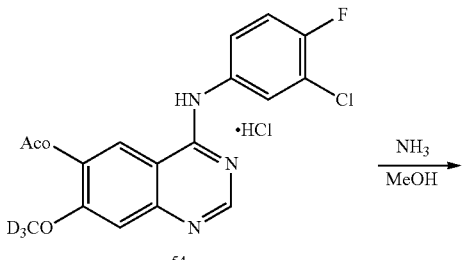
54

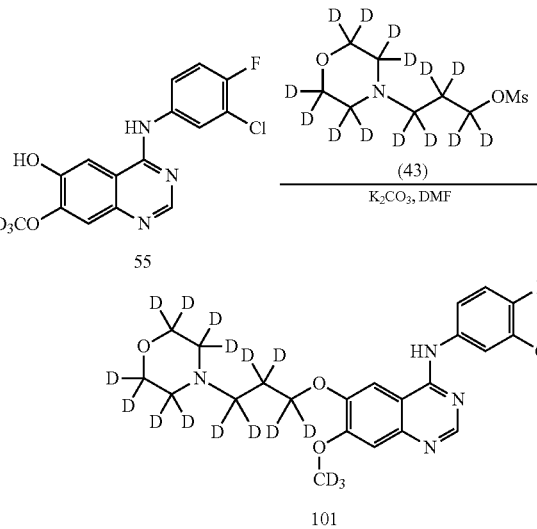
101

Synthesis of Methyl 3-methoxy-4-(methoxy-$d_3$)benzoate (47). To a solution of methyl 3,4-dimethoxybenzoate 46 (25.0 g, 137.2 mmol) in THF (250 mL) was added triphenylphosphine (43.1 g, 164.6 mmol) and methanol-$d_4$ (11.2 mL, 274.4 mmol). The resulting mixture was stirred at room temperature (rt) under an argon atmosphere, then diisopropyl azodicarboxylate (33 mL, 164.6 mmol) was added dropwise and the reaction mixture was stirred for 2 h. THF was removed by distillation and the resulting mixture was partitioned between water and ethyl acetate. The organic layer was dried over $Na_2SO_4$ and concentrated in vacuo to afford the product 47 (23.0 g, 91%). MS (M+H): 200.1

Synthesis of Methyl 4-(methoxy-d₃)-5-methoxy-2-nitrobenzoate (48). A solution of 47 (30.0 g, 150.6 mmol) in acetic acid (102 mL) was added dropwise to nitric acid (32 mL, 70%) at 0-5° C. and then stirred at rt for 12 h. The resulting yellow solid was washed with ice cold water and filtered to afford 48 (35.0 g, 95%). MS (M+H): 245.

Synthesis of Methyl 2-amino-4-(methoxy-d₃)-5-methoxybenzoate (49). To a solution of 48 (36.0 g, 147.4 mmol) in dichloromethane (400 mL) and methanol (100 mL) was added nickel (II) chloride hexahydrate (10.3 g, 44.2 mmol). Sodium borohydride (18.3 g, 486.4 mmol) was added in portions at 0-5° C. over 30 minutes (min). The mixture was stirred for an additional 1 h, then was concentrated in vacuo. Cold 2N HCl (500 mL) was added to the residue and the resulting mixture was extracted with ethyl acetate. After washing with brine and drying (Na₂SO₄), the organic layer was concentrated in vacuo to afford the product 49 (25.0 g, 79%). ¹H NMR (400 MHz, DMSO-d₆) δ: 7.31 (s, 1H), 6.17 (s, 1H), 3.86 (s, 3H), 3.84 (s, 3H). MS (M+H): 215.1

Synthesis of 6-Methoxy-7-(methoxy-d₃)quinazolin-4 (3H)-one (50). A solution of 49 (17.0 g, 79.3 mmol) in formamide (170 mL) was stirred under reflux conditions for 12 h. The resultant precipitate was washed with water and filtered to afford 50 (13.5 g, 81%). ¹H NMR (400 MHz, DMSO-d₆) δ: 7.97 (s, 1H), 7.42 (s, 1H), 7.11 (s, 1H), 3.85 (s, 3H). MS (M+H): 210.

Synthesis of 6-Hydroxy-7-(methoxy-d₃)quinazolin-4 (3H)-one (51). A mixture of 50 (7.00 g, 33.4 mmol) and L-methionine (5.60 g, 35.4 mmol) was dissolved in methanesulfonic acid (50 mL), heated to reflux and stirred for 4 h. Crushed ice/water was added to the mixture, then NaOH (40% water solution) was added slowly (pH~7) resulting in a white precipitate. The solid was filtered through a sintered glass funnel, washed with water and dried under vacuum. The resulting amorphous solid was crystallized from MeOH to afford 51 (2.10 g, 32%). ¹H NMR (400 MHz, DMSO-d₆) δ: 11.94 (s, 1H), 9.81 (s, 1H), 7.90 (s, 1H), 7.36 (s, 1H), 7.07 (s, 1H). MS (M+H): 196.

Synthesis of 7-(Methoxy-d₃)-4-oxo-3,4-dihydroquinazolin-6-yl acetate (52). A suspension of 51 (2.10 g, 10.7 mmol), pyridine (2.2 mL) and DMAP (catalytic amount) in acetic anhydride (16.8 mL) was heated to 100° C. and stirred under an argon atmosphere for 6 h. Crushed ice/water was added and the resulting white precipitate was filtered, washed with water and dried to afford the product 52 (2.00 g, 80%). ¹H NMR (400 MHz, DMSO-d₆) δ: 12.0 (s, 1H), 8.07 (s, 1H), 7.63 (s, 1H), 7.26 (s, 1H), 2.28 (s, 3H).

Synthesis of 4-Chloro-7-(methoxy-d₃)quinazolin-6-yl acetate (53). To a solution of 52 (2.00 g, 8.4 mmol) in CHCl₃ (20 mL) was added a catalytic amount of DMF. The resulting mixture was stirred at 0° C. under an argon atmosphere. Oxalyl chloride (2.1 ml) was added dropwise and the mixture was heated to 60° C. and stirred for 5 h. The reaction was quenched by the addition of satd NaHCO₃ solution. The organic layer was separated, dried over Na₂SO₄ and concentrated in vacuo to afford 53 (2.00 g, 95%). MS (M+H): 256.

Synthesis of 4-(3-Chloro-4-fluorophenylamino)-7-(methoxy-d₃)quinazolin-6-yl acetate hydrochloride (54). A solution of 53 (2.00 g, 7.8 mmol) and 3-chloro-4-fluorophenylamine (1.10 g, 7.8 mmol) in i-prOH (20 mL) was stirred and heated to 90° C. under an argon atmosphere for 5 h. The reaction mixture was cooled to rt and the precipitate was filtered through a sintered glass funnel and dried under vacuum to afford 54 as a white powder (3.00 g, 96%). ¹H NMR (400 MHz, DMSO-d₆)δ: 10.7 (bs, 1H), 8.8 (s, 1H), 8.5 (s, 1H), 8.1 (m, 1H), 7.8 (m, 1H), 7.55 (m, 1H), 7.4 (m, 1H), 2.4 (s, 3H). MS (M+H): 365.

Synthesis of 4-(3-Chloro-4-fluorophenylamino)-7-methoxyquinazolin-6-ol (55). A solution of 54 (3.00 g, 7.4 mmol) in NH₃/MeOH (3 mL/50 mL) was stirred at rt for 24 h. The resulting white precipitate was filtered, washed with water and dried at 50° C. to afford 55 as a white solid (2.00 g, 83%). ¹H NMR (400 MHz, DMSO-d₆) δ: 9.7 (s, 1H), 9.5 (s, 1H), 8.5 (s, 1H), 8.1 (m, 1H), 7.9 (m, 1H), 7.8 (m, 1H), 7.4 (m, 1H), 7.2 (m, 1H). MS (M+H): 323.

Synthesis of N-(3-Chloro-4-fluorophenyl)-7-(methoxy-d₃)-6-(3-(morpholino-d₈)propoxy-d₆)quinazolin-4-amine (101). A solution of 55 (0.50 g, 1.54 mmol), potassium carbonate (0.42 g, 3.08 mmol), and KI (0.10 g) in DMF (10 mL) was stirred at 40° C. for 20 min, followed by the addition of 43 (1.10 g, 4.64 mmol). This mixture was heated to 80° C. and stirred for 6 h under an argon atmosphere. DMF was removed in vacuo and the crude mixture was purified by silica gel column chromatography (4:1 dichloromethane and methanol) to afford 101 (0.25 g, 35%). ¹H NMR (400 MHz, DMSO-d₆) δ: 9.51 (s, 1H), 8.48 (s, 1H),8.08-8.13 (m, 1H), 7.45-7.82 (m, 2H), 7.35-7.45 (m, 1H), 7.19 (s, 1H). MS (M+H): 464.2.

Example 5

Synthesis of N-(3-Chloro-4-fluorophenyl)-7-(methoxy-d₃)-6-(3-morpholino(propoxy-d₆))quinazolin-4-amine (102)

Compound 102 was prepared as outlined in Scheme 5 above with the exception that intermediate 43 was replaced with intermediate 44. Details of the synthesis are set forth below.

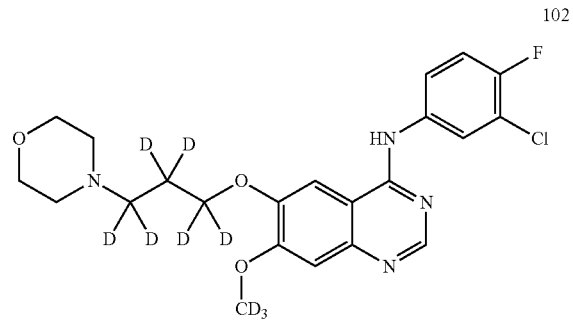 [SMILES: [2H]C([2H])([2H])Oc1cc2ncnc(Nc3ccc(F)c(Cl)c3)c2cc1OC([2H])([2H])C([2H])([2H])C([2H])([2H])N1CCOCC1]

Synthesis of N-(3-Chloro-4-fluorophenyl)-7-(methoxy-d₃)-6-(3-morpholino(propoxy-d₆))quinazolin-4-amine (102). A solution of 55 (0.50 g, 1.55 mmol), potassium carbonate (0.43 g, 3.1 mmol), and KI (0.10 g) in DMF (10 mL) was stirred at 40° C. for 20 min, followed by addition of 44 (1.00 g, 4.65 mmol). The resulting mixture was heated to 80° C. and stirred for 6 h under an argon atmosphere. DMF was removed in vacuo and the crude mixture was purified by silica gel column chromatography (4:1 ethyl acetate and methanol) to afford 102 (0.36 g, 51%). ¹H NMR (400 MHz, DMSO-d₆) δ: 9.60 (s, 1H), 8.60 (s, 1H), 8.10 (m, 1H), 7.86 (s, 1H), 7.76-7.80 (m, 1H), 7.44 (t, 1H), 7.23 (s, 1H), 4.00-4.20 (m, 2H), 3.50-3.80 (m, 4H), 3.00-3.45 (m, 2H). MS (M+H): 456.

Example 6

Synthesis of N-(3-Chloro-4-fluorophenyl)-7-(methoxy-d₃)-6-(3-morpholinopropoxy)quinazolin-4-amine (104)

Compound 104 was prepared as outlined in Scheme 5 above replacing intermediate 43 with intermediate 45. Details of the synthesis are set forth below.

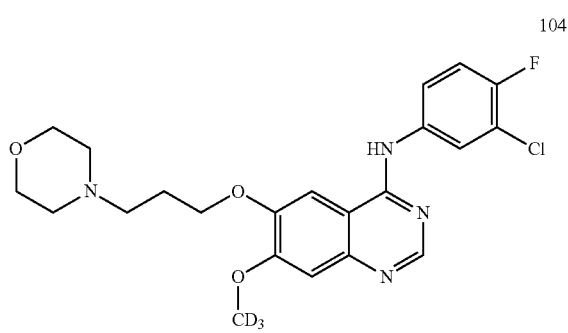 [SMILES: [2H]C([2H])([2H])Oc1cc2ncnc(Nc3ccc(F)c(Cl)c3)c2cc1OCCCN1CCOCC1]

104

Synthesis of N-(3-Chloro-4-fluorophenyl)-7-(methoxy-d$_3$)-6-(3-morpholinopropoxy)quinazolin-4-amine (104). A solution of 55 (0.40 g, 1.24 mmol) and potassium carbonate (0.92 g, 6.6 mmol) in DMF (10 mL) was stirred at 40° C. for 20 min followed by the addition of 45 (0.20 g, 1.39 mmol). The resulting mixture was heated to 80° C. and stirred for 6 h under an argon atmosphere. DMF was removed in vacuo and the crude mixture was purified by silica gel column chromatography (4:1 ethyl acetate and methanol) to afford 104 (0.32 g, 58%). $^1$H NMR (400 MHz, DMSO-d$_6$) δ: 9.60 (s, 1H), 8.60 (s, 1H), 8.20 (m, 1H), 7.80 (m, 2H), 7.40 (t, 1H), 7.30 (s, 1H), 4.20 (t, 2H), 3.50-3.80 (m, 4H), 2.45 (m, 4H), 1.93-2.00 (m, 2H). MS (M+H): 450.

Evaluation of Metabolic Stability

Evaluation of Metabolic Stability. Certain in vitro liver metabolism studies have been described previously in the following references, each of which is incorporated herein in their entirety: Obach, R S, Drug Metab Disp, 1999, 27:1350; Houston, J B et al, Drug Metab Rev, 1997, 29:891; Houston, J B, Biochem Pharmacol, 1994, 47:1469; Iwatsubo, T et al, Pharmacol Ther, 1997, 73:147; and Lave, T, et al, Pharm Res, 1997, 14:152.

Microsomal Assay: Human liver microsomes (20 mg/mL) were obtained from Xenotech, LLC (Lenexa, Kans.). βnicotinamide adenine dinucleotide phosphate, reduced form (NADPH), magnesium chloride (MgCl$_2$), and dimethyl sulfoxide (DMSO) were purchased from SigmaAldrich. The incubation mixtures were prepared according to Table 2:

TABLE 2

| Reaction Mixture Composition for Human Liver Microsome Study | |
|---|---|
| Liver Microsomes | 3.0 mg/mL |
| Potassium Phosphate, pH 7.4 | 100 mM |
| Magnesium Chloride | 10 mM |

Determination of Metabolic Stability: Two aliquots of this reaction mixture were used for a compound of this invention. The aliquots were incubated in a shaking water bath at 37° C. for 3 minutes. The test compound was then added into each aliquot at a final concentration of 0.5 μM. The reaction was initiated by the addition of cofactor (NADPH) into one aliquot (the other aliquot lacking NADPH served as the negative control). Both aliquots were then incubated in a shaking water bath at 37° C. Fifty microliters (50 μL) of the incubation mixtures were withdrawn in triplicate from each aliquot at 0, 5, 10, 20, and 30 minutes and combined with 50 μL of ice-cold acetonitrile to terminate the reaction. The same procedure was followed for gefitinib and 7-ethoxycoumarin, the positive control. Testing was done in triplicate.

Data analysis: The in vitro half-lives ($t_{1/2}$s) for test compounds were calculated from the slopes of the linear regression of % parent remaining (ln) vs incubation time relationship using the following formula:

in vitro $t_{1/2}$=0.693/k, where k=[slope of linear regression of % parent remaining(ln)vs incubation time]

Data analysis was performed using Microsoft Excel Software.

The metabolic stability of compounds of Formula A or I was tested using pooled liver microsomal incubations. Full scan LCMS analysis was then performed to detect major metabolites. Samples of the test compounds, exposed to pooled human liver microsomes, were analyzed using HPLCMS (or MS/MS) detection. For determining metabolic stability, multiple reaction monitoring (MRM) was used to measure the disappearance of the test compounds. For metabolite detection, Q1 full scans were used as survey scans to detect the major metabolites.

The data is depicted in Table 3 and FIG. 1.

TABLE 3

| In vitro $t_{1/2}$ s 101, 102, and 104. | | | | | |
|---|---|---|---|---|---|
| Compound No. | | | $t_{1/2}$ (min) | | |
| Experiment No. | 1 | 2 | 3 | Ave | SD |
| Gefitinib | 19.4 | 17.6 | 19.8 | 18.9 | 1.2 |
| 101 | 24.3 | 23.8 | 23.1 | 23.7 | 0.6 |
| 102 | 22.5 | 20.8 | 21.8 | 21.7 | 0.8 |
| 104 | 22.5 | 20.8 | 21.8 | 21.7 | 0.8 |

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention. All the patents, journal articles and other documents discussed or cited above are herein incorporated by reference.

I claim:

1. A method of modulating the activity of an epidermal growth factor receptor tyrosine kinase in a cell comprising contacting the cell with a compound of Formula A

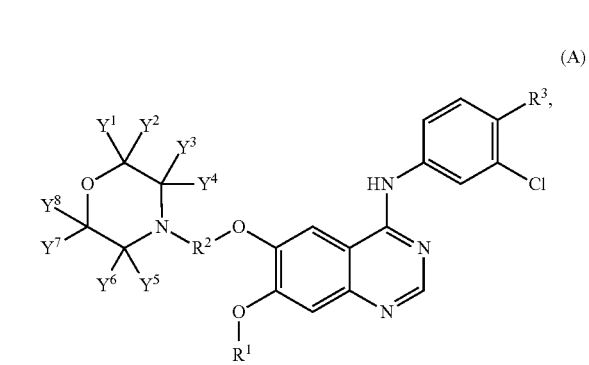

(A)

or a pharmaceutically acceptable salt thereof, wherein the compound is selected from any one of the compounds depicted in the following Table:

| Cmpd | $Y^1 = Y^2$ | $Y^3 = Y^4$ | $Y^5 = Y^6$ | $Y^7 = Y^8$ | $R^1$ | $R^2$ | $R^3$ |
|---|---|---|---|---|---|---|---|
| 101 | D | D | D | D | $CD_3$ | $CD_2CD_2CD_2$ | F |
| 102 | H | H | H | H | $CD_3$ | $CD_2CD_2CD_2$ | F |
| 104 | H | H | H | H | $CD_3$ | $CH_2CH_2CH_2$ | F |
| 108 | D | D | D | D | $CD_3$ | $CD_2CD_2CD_2$ | H |
| 109 | H | H | H | H | $CD_3$ | $CD_2CD_2CD_2$ | H |
| 110 | D | D | D | D | $CD_3$ | $CH_2CH_2CH_2$ | H |
| 111 | H | H | H | H | $CD_3$ | $CH_2CH_2CH_2$ | H |
| 112 | D | D | D | D | $CD_3$ | $CD_2CD_2CD_2$ | H |
| 113 | H | H | H | H | $CD_3$ | $CD_2CD_2CD_2$ | H |
| 114 | D | D | D | D | $CD_3$ | $CH_2CH_2CH_2$ | H |
| 115 | D | D | D | D | $CD_3$ | $CD_2CD_2CD_2$ | OH |
| 116 | H | H | H | H | $CD_3$ | $CD_2CD_2CD_2$ | OH |
| 117 | D | D | D | D | $CD_3$ | $CH_2CH_2CH_2$ | OH |
| 118 | H | H | H | H | $CD_3$ | $CH_2CH_2CH_2$ | OH |
| 119 | D | D | D | D | $CD_3$ | $CD_2CD_2CD_2$ | OH |
| 120 | H | H | H | H | $CD_3$ | $CD_2CD_2CD_2$ | OH |
| 121 | D | D | D | D | $CD_3$ | $CH_2CH_2CH_2$ | OH |
| 122 | D | D | D | D | $CD_3$ | $CD_2CD_2CD_2$ | $OCD_3$ |
| 123 | H | H | H | H | $CD_3$ | $CD_2CD_2CD_2$ | $OCD_3$ |
| 124 | D | D | D | D | $CD_3$ | $CH_2CH_2CH_2$ | $OCD_3$ |
| 125 | H | H | H | H | $CD_3$ | $CH_2CH_2CH_2$ | $OCD_3$ |
| 126 | D | D | D | D | $CD_3$ | $CD_2CD_2CD_2$ | $OCD_3$ |
| 127 | H | H | H | H | $CD_3$ | $CD_2CD_2CD_2$ | $OCD_3$ |
| 128 | D | D | D | D | $CD_3$ | $CH_2CH_2CH_2$ | $OCD_3$ |
| 129 | D | D | D | D | $CD_3$ | $CD_2CD_2CD_2$ | $OCH_3$ |
| 130 | H | H | H | H | $CD_3$ | $CD_2CD_2CD_2$ | $OCH_3$ |
| 131 | D | D | D | D | $CD_3$ | $CH_2CH_2CH_2$ | $OCH_3$ |
| 132 | H | H | H | H | $CD_3$ | $CH_2CH_2CH_2$ | $OCH_3$ |
| 133 | D | D | D | D | $CD_3$ | $CD_2CD_2CD_2$ | $OCH_3$ |
| 134 | H | H | H | H | $CD_3$ | $CD_2CD_2CD_2$ | $OCH_3$ |
| 135 | D | D | D | D | $CD_3$ | $CH_2CH_2CH_2$ | $OCD_3$ |
| 136 | D | D | D | D | $CD_3$ | $CD_2CD_2CD_2$ | Cl |
| 137 | H | H | H | H | $CD_3$ | $CD_2CD_2CD_2$ | Cl |
| 138 | D | D | D | D | $CD_3$ | $CH_2CH_2CH_2$ | Cl |
| 139 | H | H | H | H | $CD_3$ | $CH_2CH_2CH_2$ | Cl |
| 140 | D | D | D | D | $CD_3$ | $CD_2CD_2CD_2$ | Cl |
| 141 | H | H | H | H | $CD_3$ | $CD_2CD_2CD_2$ | Cl |
| 142 | D | D | D | D | $CD_3$ | $CH_2CH_2CH_2$ | Cl |
| 143 | D | D | D | D | $CD_3$ | $CD_2CD_2CD_2$ | Br |
| 144 | H | H | H | H | $CD_3$ | $CD_2CD_2CD_2$ | Br |
| 145 | D | D | D | D | $CD_3$ | $CH_2CH_2CH_2$ | Br |
| 146 | H | H | H | H | $CD_3$ | $CH_2CH_2CH_2$ | Br |
| 147 | D | D | D | D | $CD_3$ | $CD_2CD_2CD_2$ | Br |
| 148 | H | H | H | H | $CD_3$ | $CD_2CD_2CD_2$ | Br |
| 149 | D | D | D | D | $CD_3$ | $CH_2CH_2CH_2$ | Br. |

\* \* \* \* \*